(12) United States Patent
O'Donnell

(10) Patent No.: US 9,867,587 B2
(45) Date of Patent: Jan. 16, 2018

(54) METHOD AND SYSTEM FOR CONTROLLING X-RAY RADIATION DOSAGE APPLIED IN AN X-RAY CT SYSTEM

(71) Applicant: Siemens Medical Solutions USA, Inc., Malvern, PA (US)

(72) Inventor: Thomas O'Donnell, New York, NY (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 289 days.

(21) Appl. No.: 14/663,510

(22) Filed: Mar. 20, 2015

(65) Prior Publication Data

US 2016/0270756 A1    Sep. 22, 2016

(51) Int. Cl.
*A61B 6/00* (2006.01)
*A61B 6/03* (2006.01)

(52) U.S. Cl.
CPC .............. *A61B 6/542* (2013.01); *A61B 6/032* (2013.01); *A61B 6/502* (2013.01)

(58) Field of Classification Search
CPC ......... A61B 6/032; A61B 6/542; A61B 6/544; A61B 6/405; A61B 6/4241; A61B 6/469; A61B 6/488; A61B 6/027; A61B 6/107; A61B 6/12; A61B 6/14; A61B 6/4035; A61B 6/4482; A61B 6/4488; A61B 6/482; A61B 6/501; A61B 6/583; A61B 6/502; A61B 6/4233; A61B 6/548; A61B 6/4283; A61B 6/06; A61B 6/4208; A61B 6/4291; A61B 6/5241; H05G 1/44; H05G 1/30; H05G 1/36; H05G 1/46; A61K 2300/00; A61K 31/337; A61K 31/675; A61K 31/704; A61K 39/39558; C12C 1/6841; C12C 1/6886; C12C 2600/106; H04N 5/32; H04N 5/2351
USPC .................................... 378/4, 16, 19, 62, 97
See application file for complete search history.

(56) References Cited

U.S. PATENT DOCUMENTS

| | | | |
|---|---|---|---|
| 6,850,588 B2 * | 2/2005 | Arenson | A61B 6/107 378/108 |
| 6,990,171 B2 * | 1/2006 | Toth | A61B 6/032 378/158 |
| 8,031,831 B2 * | 10/2011 | Zou | A61B 6/032 378/108 |
| 2009/0041188 A1 * | 2/2009 | Keall | A61N 5/1042 378/65 |
| 2012/0243657 A1 * | 9/2012 | O'Loughlin | A61B 6/032 378/16 |

* cited by examiner

*Primary Examiner* — Irakli Kiknadze

(57) ABSTRACT

A method of controlling radiation dosage of an X-Ray CT system includes applying radiation to a patient along a z-axis in an x-y plane at angles during rotations around the z-axis. The method also includes acquiring projections of the patient to reconstruct a 3D image of the patient's anatomy and controlling a dosage of the radiation by causing a same dosage of the radiation to be applied in the x-y plane to a posterior of the patient and to an anterior of the patient at a first portion along the length of the z-axis and causing a varied dosage of the radiation to be applied in the x-y plane at a second portion along the length of the z-axis. The varied dosage includes a first dosage applied to the posterior and a second dosage applied to the anterior that is less than the first dosage.

18 Claims, 8 Drawing Sheets

METHOD AND SYSTEM FOR CONTROLLING X-RAY RADIATION DOSAGE APPLIED IN AN X-RAY CT SYSTEM

TECHNOLOGY FIELD

The present application relates generally to methods and systems for providing a 3D image of patient anatomy using X-Ray computer assisted tomography (X-Ray CT), and in particular, to controlling X-Ray radiation dosage applied in an x-y plane along a length of the patient based on different radiosensitive portions of the patient anatomy.

BACKGROUND

Medical imaging may be used to create images of the human body. Some medical imaging techniques include the use of X-Ray radiation, such as X-Ray CT. X-Ray CT systems apply X-Ray radiation to the patient anatomy and provide X-Ray projections to reconstruct 3D images of portions of the patient anatomy. Typically, higher dosages of X-Ray radiation provide a more defined image quality. Higher dosages of the X-Ray radiation are also more harmful to the anatomy.

Some conventional X-Ray CT systems reduce X-Ray radiation dosage along the z-length (along length of the z-axis extending along the length of the patient) of the scan during anterior view of the patient to lessen the exposure to radiosensitive organs such as the eyes, thyroid and breasts. These systems compensate for the reduced X-Ray radiation dosage with higher X-Ray radiation dosage during posterior views of the patient along the z-length of the scan to provide better image quality. A continuing need exists, however, for better and more efficient X-Ray CT systems.

SUMMARY

Embodiments provide a method of controlling radiation dosage of an X-Ray computer assisted tomography (CT) system. The method includes applying X-Ray radiation to anatomy of a patient along a length of a z-axis in an x-y plane at a plurality of angles during each of one or more 360 degree rotations around the z-axis. The z-axis extends along a length of the patient and intersects the x-y plane. The method also includes acquiring X-Ray projections of the anatomy of the patient to reconstruct a three dimensional (3D) image of the anatomy. The method further includes controlling a dosage of the X-Ray radiation applied to the anatomy of the patient by causing a same dosage of the X-Ray radiation to be applied in the x-y plane to a posterior of the patient and to an anterior of the patient at a first portion along the length of the z-axis and causing a varied dosage of the X-Ray radiation to be applied in the x-y plane at a second portion along the length of the z-axis. The varied dosage includes a first dosage applied to the posterior of the patient and a second dosage applied to the anterior of the patient. The second dosage applied to the anterior of the patient is less than the first dosage applied to the posterior of the patient.

According to an embodiment, the method further includes determining a location of a radiosensitive portion of the anatomy of the patient along the length of the z-axis and causing the varied dosage of the X-Ray radiation to be applied in the x-y plane at the second portion along the length of the z-axis based on the determined location of the radiosensitive portion along the length of the z-axis.

According to another embodiment, the location of the radiosensitive portion of the anatomy of the patient along the length of the z-axis is determined from a corresponding location of the radiosensitive portion in an image acquired from a topogram of the patient prior to applying the X-Ray radiation to the anatomy of the patient in the x-y plane and along the z-axis.

In one embodiment, the location of the radiosensitive portion of the anatomy of the patient along the length of the z-axis is determined from a corresponding location of the radiosensitive portion in one or more images acquired from a camera.

In another embodiment, the location of the radiosensitive portion of the anatomy of the patient along the length of the z-axis is determined from a location of one or more other portions of the anatomy of the patient.

In yet another embodiment, controlling the dosage of the X-Ray radiation applied to the anatomy of the patient further includes determining the location of the radiosensitive portion of the anatomy along the x-y plane and causing the varied dosage of the X-Ray radiation to be applied along the x-y plane based on the determined location of the radiosensitive portion of the anatomy along the x-y plane.

In an aspect of an embodiment, the method further includes causing the varied dosage of the X-Ray radiation to be applied in the x-y plane for a range of degrees of the 360 degrees around the z-axis of rotation based on the determined location of the radiosensitive portion of the anatomy along the x-y plane.

According to an embodiment, the X-Ray CT system is one of: (i) a non-spiral X-Ray CT system; and (ii) a spiral X-Ray CT system. The same dosage of the X-Ray radiation is applied in the x-y plane perpendicular to the z-axis and the varied dosage of the X-Ray radiation is applied in the x-y plane perpendicular to the z-axis.

According to another embodiment, the X-Ray CT system is a spiral X-Ray CT system. The same dosage of the X-Ray radiation is applied in the x-y plane at an angle non-perpendicular to the z-axis and the varied dosage of the X-Ray radiation is applied in the x-y plane at an angle non-perpendicular to the z-axis Embodiments provide an X-Ray CT system that includes a gantry having an opening configured to receive a patient and a tube-detector system configured to rotate 360 degrees around a z-axis extending along a length of the patient. The tube-detector system of the gantry includes an X-Ray tube configured to apply X-Ray radiation to anatomy of the patient in an x-y plane at a plurality of angles during each of one or more 360 degree rotations along a length of the z-axis that intersects the x-y plane and an X-Ray detector disposed opposite the X-Ray tube and configured to detect the X-Ray radiation. The X-Ray CT system also includes an image processor configured to acquire and process X-Ray projections of anatomy of the patient provided by the tube-detector system to reconstruct a three dimensional (3D) image of the anatomy of the patient and a processor configured to control a dosage of the X-Ray radiation applied to the anatomy of the patient by causing a same dosage of the X-Ray radiation to be applied in the x-y plane to a posterior of the patient and to an anterior of the patient at a first portion along the length of the z-axis and causing a varied dosage of the X-Ray radiation to be applied in the x-y plane at a second portion along the length of the z-axis. The varied dosage includes a first dosage applied to the posterior of the patient and a second dosage applied to the anterior of the patient, the second dosage applied to the anterior of the patient being less than the first dosage applied to the posterior of the patient.

Embodiments provide an article of manufacture for controlling radiation dosage of an X-Ray CT system. The article of manufacture includes a non-transitory, tangible computer-readable medium holding computer-executable instructions for performing a method that includes applying X-Ray radiation to anatomy of a patient along the length of a z-axis in an x-y plane at a plurality of angles during each of one or more 360 degree rotations around the z-axis. The z-axis extends along a length of the patient and intersecting the x-y plane. The method also includes acquiring X-Ray projections of the anatomy of the patient to reconstruct a three dimensional (3D) image of the anatomy and controlling a dosage of the X-Ray radiation applied to the anatomy of the patient by causing a same dosage of the X-Ray radiation to be applied in the x-y plane to a posterior of the patient and to an anterior of the patient at a first portion along the length of the z-axis and causing a varied dosage of the X-Ray radiation to be applied in the x-y plane at a second portion along the length of the z-axis. The varied dosage comprising a first dosage applied to the posterior of the patient and a second dosage applied to the anterior of the patient, the second dosage applied to the anterior of the patient being less than the first dosage applied to the posterior of the patient.

BRIEF DESCRIPTION OF THE DRAWING

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF EXEMPLARY EMBODIMENTS

Figure 1:
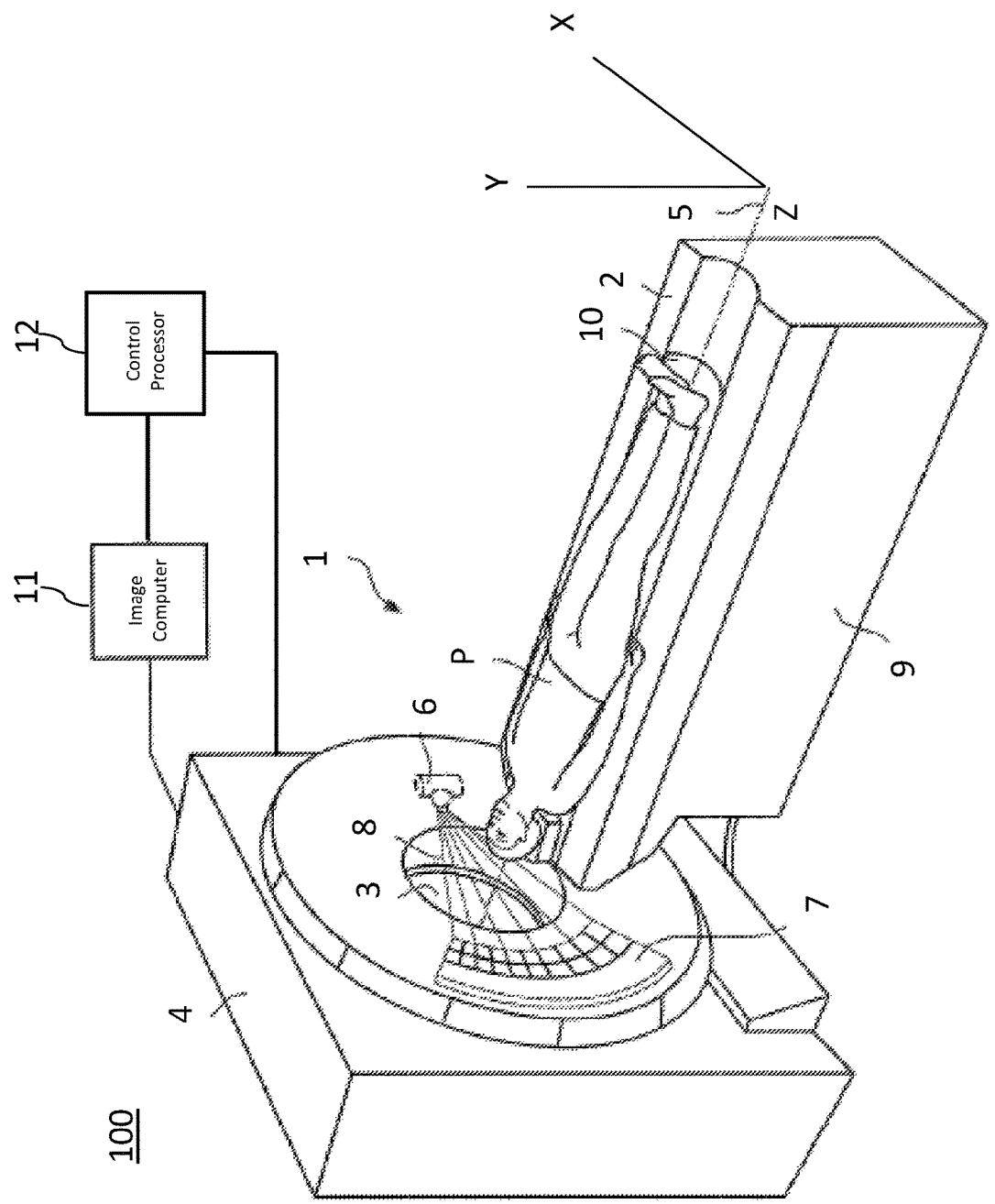
FIG. 1 is a diagram illustrating an exemplary X-Ray CT system that may be used with embodiments disclosed herein.

While some conventional X-Ray CT systems reduce the X-Ray radiation dosage during anterior view of the patient to lessen the exposure to radiosensitive organs, this reduced dosage extends along the full length of the patient. That is, the reduced dosage extends along the full z-length of the scan. These radiosensitive organs do not, however, extend the full z-length of the scan. For example, the lengths of some radiosensitive organs, such as the eyes, extend along small portions of the z-length. Further, these conventional systems continuously apply the reduced dosage uniformly (e.g., for the same ranges of degrees) in the x-y plane along the z-length of the scan during the anterior view of the patient.

Embodiments provide X-Ray CT systems and methods that control the X-Ray radiation dosage applied within an x-y plane along the z-length based on determined locations of radiosensitive portions (e.g., organs) of the patient's anatomy. Embodiments provide systems and methods that determine locations of the radiosensitive portions of the patient's anatomy along the z-length and apply reduced X-Ray radiation dosage along the z-length of the scan to the anterior of the anatomy based on the determined locations of the radiosensitive portions. Embodiments determine locations of radiosensitive portions (e.g., eyes) of a patient's anatomy from images acquired from topograms of the patient prior to the X-Ray CT scan. Embodiments determine locations of radiosensitive portions (e.g., breasts) of a patient's anatomy from images acquired from a camera (e.g., a structured light camera). In some embodiments, other portions of anatomy (e.g., neck) may be used to indicate locations of radiosensitive portions (e.g., thyroid).

Embodiments provide systems and methods that determine locations of radiosensitive portions along the x-y plane of a patient's anatomy and apply varied dosages (increased and reduced dosages) of X-Ray radiation to the patient's anatomy along the x-y plane based on the determined locations of radiosensitive portions. Embodiments apply the varied dosages along the x-y plane at different ranges of degrees in the x-y plane along the z-length of the scan. Embodiments apply the varied dosages along the x-y plane at different angles (e.g., angles relative to the z-axis) in the x-y plane along the z-length of the scan.

In some embodiments, a non-spiral CT system may be used which records single images or scans successively at discrete positions. In these embodiments, the z-axis extending along a length of the patient is perpendicular to the x-y plane.

In other embodiments, a spiral (also known as helical) CT system may be used which includes continuous tube and detector rotation. In a spiral CT system, the patient is continuously moved along the z-axis and a continuous set of data is recorded without interruption. In some aspects of spiral scanning, such as adaptive multiple plane reconstruction (AMPR), image planes are not perpendicular to the z-axis. Rather, the image planes are tilted to match the spiral path of the focal spot. Accordingly the z-axis extending along a length of the patient is not perpendicular to the x-y plane.

FIG. 1 is a diagram illustrating an exemplary X-Ray CT system 100 that may be used with embodiments disclosed herein. Shown in FIG. 1 is a computed tomography apparatus 1 that includes a patient bed 2 to support a patient P to be examined. The computed tomography apparatus 1 also includes a gantry 4 with a tube-detector system configured to rotate around a system axis 5. In the embodiments described herein, the system axis corresponds to a z-axis, for example as shown in FIG. 1. The z-axis is perpendicular to an x-y plane defined by the x-axis and the y-axis shown in FIG. 1. The tube-detector system has an X-Ray tube 6 and an X-ray detector unit 7 situated opposite one another. In operation, X-Ray radiation 8 emanates from the X-Ray tube 6 in the direction of the X-Ray detector unit 7 and is detected by the detector unit 7.

The patient bed 2 has a bed base 9 on which is arranged a patient support plate 10 provided to actually support the patient P. The patient support plate 10 is adjustable relative to the bed base 9 such that the patient support plate 10 with the patient P thereon can be introduced into the opening 3 of the gantry 4 to acquire X-Ray projections of the patient P, for example for a topogram, a non-spiral CT scan or for a spiral CT scan.

The computational processing of the X-Ray projections, for example the generation of a topogram, a slice image or the reconstruction of a volume data set of a body region or tissue of the patient P based on the X-Ray projections, takes place with an image computer 11 (schematically shown) of the computed tomography apparatus 1. The computed tomography apparatus 1 may also include one or more computers (not shown) for operation and control of the computer tomography apparatus 1. Computers may be separate computers or may be integrated into the computed tomography apparatus 1.

A topogram may be performed prior to applying the X-Ray radiation for 360 degrees in the spiral scan. During a topogram, the X-Ray emitter is typically in front of the patient and takes a regular X-Ray which appears on the CT scan and console. The image from the topogram is typically used by a technician to determine parameters or settings of the spiral scan for a particular patient. Embodiments described herein utilize images from topograms to determine location of a radiosensitive portion of the anatomy, as described in more detail below.

During the CT scan (the spiral scan), the X-Ray tube 6 may rotate 360 degrees around the patient and apply X-Ray Radiation from a plurality of angles in the 360 degrees, providing X-Ray projections used to reconstruct a 3D image of the patient P. For example, in one embodiment, X-Ray tube 6 may be located above the patient P and may begin applying X-Ray radiation to the anterior portion (the top portion facing away from the table) of the patient. The X-Ray tube 6 may then rotate (in either direction) to a side of the patient P. The X-Ray tube 6 may then rotate to behind the patient P where X-Ray radiation is applied to the posterior portion (the portion facing toward the table) of the patient P. The X-Ray tube 6 may then continue to rotate to the opposite side of the patient before reaching the beginning location above the patient P. The beginning point and end point of each 360 degree rotation described above is merely exemplary. Embodiments may include beginning points and end points anywhere along the 360 degrees of rotation around the z-axis 5.

The system 100 may also include an image processor, such as reconstruction computer 11, that is configured to acquire and process the X-Ray projections of the anatomy of the patient P provided by the tube-detector system (e.g., X-Ray tube 6 and an X-ray detector unit 7) to reconstruct the three dimensional (3D) image of the anatomy of the patient P.

The system 100 may also include a control processor 12 configured to control a dosage of the X-Ray radiation applied to the anatomy of the patient. Any of the dosages and the changes in dosages described in the embodiments herein may be controlled by a processor by varying one or more parameters of an X-Ray CT system. The parameters include but are not limited to, a tube current, a tube voltage, a time period for applying a dosage, a range of degrees (e.g., of the 360 degree rotation around the z-axis) for applying a dosage and a length along the z-axis for applying a dosage. The control processor may also be configured to determine one or more locations of radiosensitive organs in the anatomy of a patient as described in more detail below. In some embodiments, a single controller processor may be used to determine one or more locations of radiosensitive organs in the anatomy and control the dosage applied to the patient. In other embodiments, a plurality of processors may be in communication with each other and used to determine one or more locations of radiosensitive organs in the anatomy and/or control the dosage applied to the patient.

As described above, some conventional X-Ray CT systems reduce the X-Ray radiation dosage during the anterior view (e.g., when the tube 6 is facing the anterior of the patient) of the patient and increase the dosage during the posterior view of the patient for the full z-length of the scan to lessen the exposure to radiosensitive organs disposed on or closer to the anterior of the patient. That is, these conventional X-Ray CT systems apply the same varied dosage of the X-Ray radiation for the full z-length of the scan. Because radiosensitive organs do not extend the full z-length of the scan, embodiments described herein apply the same dosage of X-Ray radiation to the posterior and anterior of the patient at one or more portions along the length of the z-axis where no radiosensitive organs are located and a varied dosage of the X-Ray radiation in the x-y plane at one or more other portions along the z-length where radiosensitive organs are located.

Figure 2:
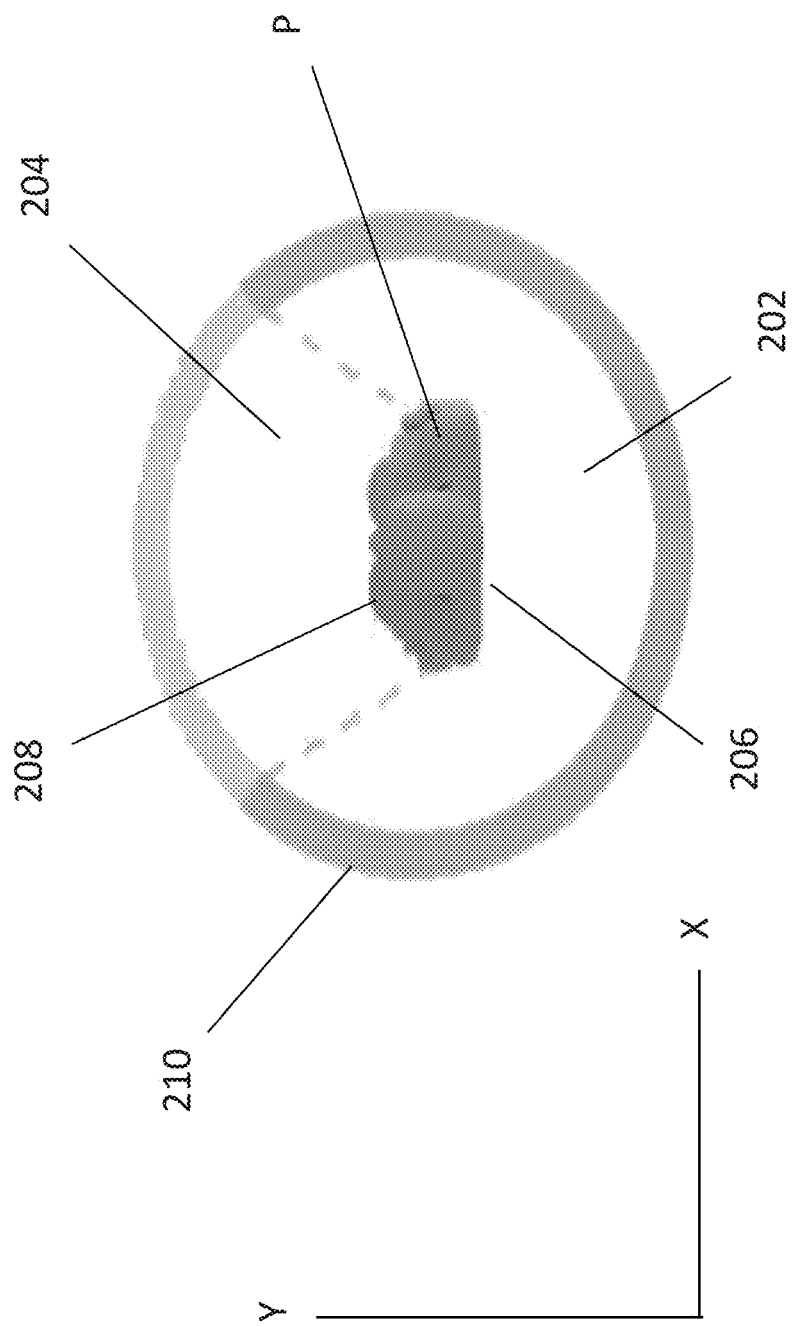
FIG. 2 is a head first view of a patient within an exemplary opening of a gantry and illustrating exemplary varied dosage regions corresponding to dosages that may be applied during a portion of the scan where radiosensitive organs are located according to embodiments disclosed herein.
Figure 3:
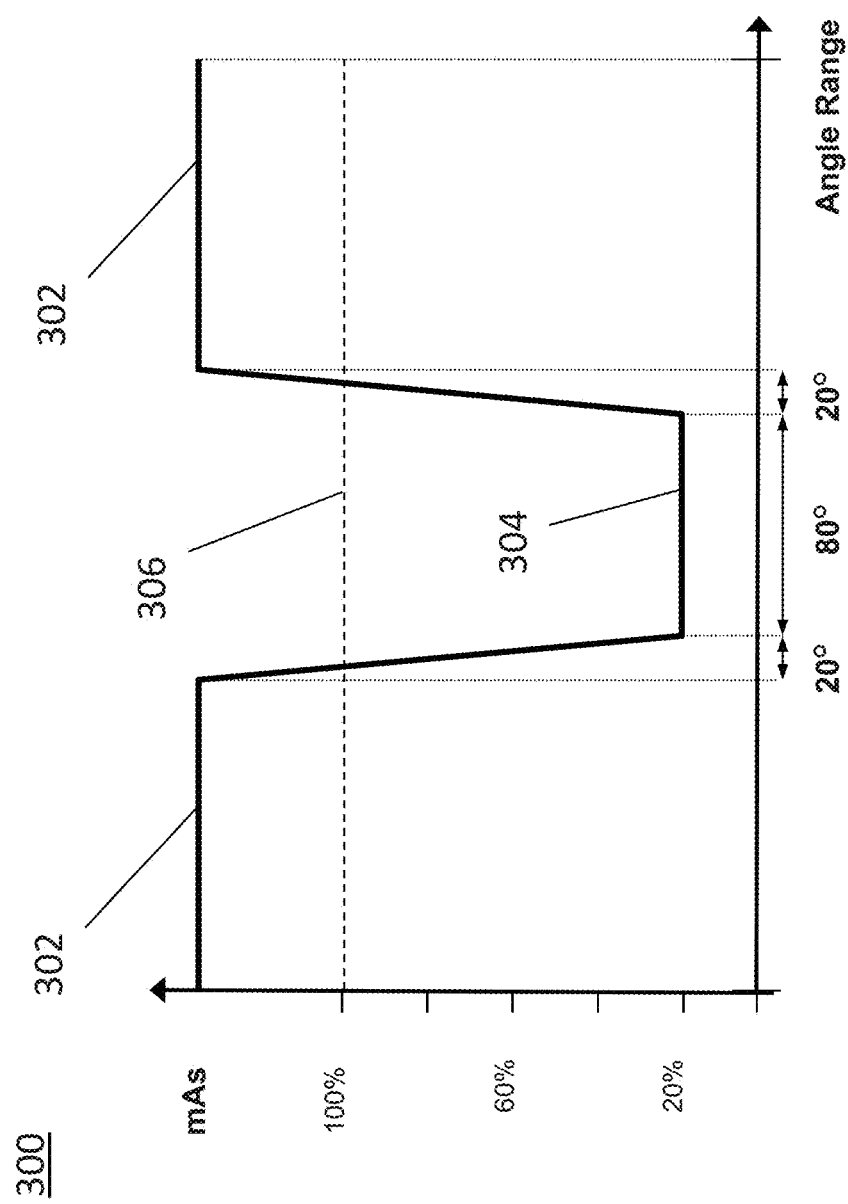
FIG. 3 is a graph illustrating the exemplary varied dosage regions shown in FIG. 2.
Figure 4:
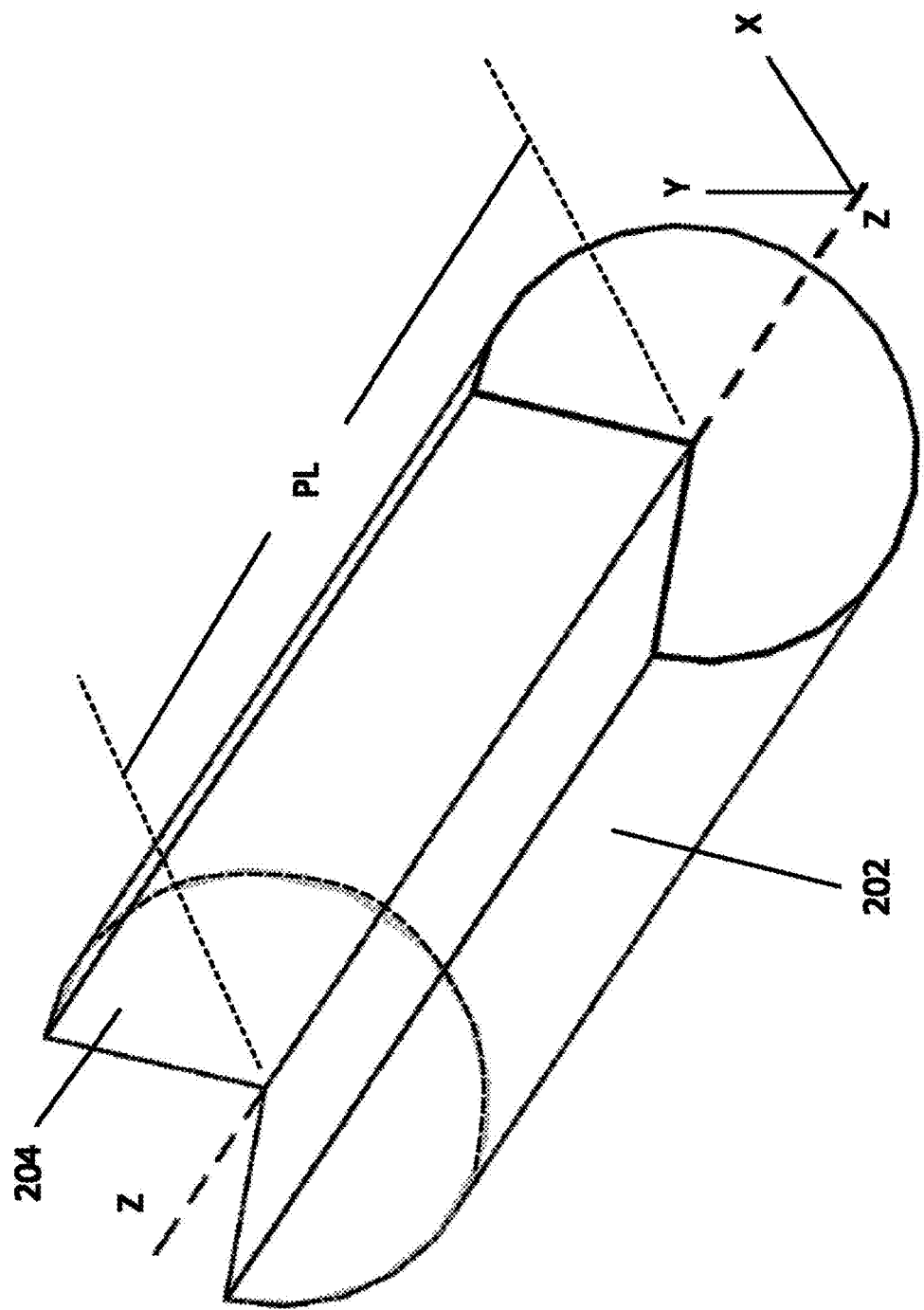
FIG. 4 is an illustration of exemplary varied dosage regions corresponding to dosages that may be applied in the x-y plane and along a portion of the z-length.

FIG. 2 through FIG. 4 are used to illustrate an exemplary varied dosage of the X-Ray radiation applied in the x-y plane along the one or more portions of the z-length where radiosensitive organs are located. FIG. 2 is a head first view of a patient P within an exemplary opening of a gantry illustrating exemplary varied dosage regions of dosages that may be applied during a portion of the scan where radiosensitive organs are located according to embodiments disclosed herein. FIG. 3 is a graph illustrating the exemplary varied dosage regions shown in FIG. 2. FIG. 4 is an illustration of exemplary varied dosage regions 202 and 204 applied in the x-y plane and along a portion of the z-length.

As shown in FIG. 2, the varied dosage may include a first dosage that is applied in a first dosage region 202 to a posterior (bottom) 206 of the patient P and a second dosage that is applied in a second dosage region 204 to the anterior (top) 208 of the patient P. The second dosage (reduced dosage) applied to the anterior 208 of the patient P is less than the first dosage. That is the level of X-Ray radiation applied to the anterior 208 of the patient P (where radiosensitive organs are closer to the radiation emitter, such as tube 6 shown in FIG. 1) is less than the level of X-Ray radiation applied to the posterior of the patient. For example, the exemplary varied dosages applied in dosage regions 202 and 204 shown in FIG. 2 may be applied at a portion along the z-length of the z-axis 5 shown in FIG. 1 where radiosensitive organs are located.

Referring to FIG. 3, the dosage changes from a first dosage level 302 to a second dosage level 304. The first dosage level 302 corresponds to a first dosage applied to the posterior 206 of the patient P and the second dosage level 302 corresponds to a second dosage applied to the anterior 208 of the patient P. The vertical axis shows the percentage of the dosage level of X-Ray radiation applied to a patient. As shown in FIG. 3, the dosage levels correspond to the amount of tube current measured in milliamps (mAs). Dosage levels may, however, correspond to other measurements, such as for example tube voltage. The horizontal axis of the graph 300 shows angle ranges (in degrees) corresponding to the dosage levels applied in the x-y plane at a plurality of angles during a 360 degree rotation of the emitter around the z-axis.

As shown in FIG. 3, the first dosage level 302 may be applied for a predetermined range of degrees or angle (e.g., angle relative to the z-axis) to the posterior 206 of the patient P. The dosage then decreases for 20 degrees during the 360 degree rotation until the second dosage level 304 is applied to the anterior 208 of the patient P. The first dosage level 302 applied to the posterior 206 is shown in FIG. 3 as above the 100% dosage level 306 to illustrate a higher dosage to compensate for the reduced second dosage level 302 applied to the anterior 208 of the patient P. The second dosage level 302 may then be applied to the anterior 206 of the patient P for 80 degrees during the 360 degree rotation until the dosage decreases for 20 degrees during the 360 degree rotation.

The dosage levels 302, 304 and 306 shown in FIG. 3 are merely exemplary. Embodiments may include varying dosages different from those shown in FIG. 3. Further, the angle ranges shown in FIG. 3 are also exemplary. Embodiments may include dosage levels applied in the x-y plane at angle ranges different from those shown in FIG. 3.

FIG. 4 shows the first dosage region 202 corresponding to a first dosage applied to a posterior 206 of the patient (not shown in FIG. 4 to better illustrate the dosage regions 202 and 204) and the second dosage region 204 corresponding to a second dosage applied to the anterior 208 of the patient. As shown in FIG. 4, the varied dosage may be applied along a portion extending a portion length PL of the length of the z-axis (z-length). The varied dosages in regions 202 and 204 applied along the portion length PL may correspond to X-Ray emissions applied in the x-y plane from one or more rotations of the emitter around the z-axis. The dosages in dosage regions 202 and 204 applied along the portion length PL may provide X-Ray projections for one or more image slices.

FIG. 5 through FIG. 8 omit the patient to better illustrate and describe various dosage regions. It is to be understood, however, that the z-axis shown in FIG. 5 through FIG. 8 extends along a length of the patient.

Figure 5:
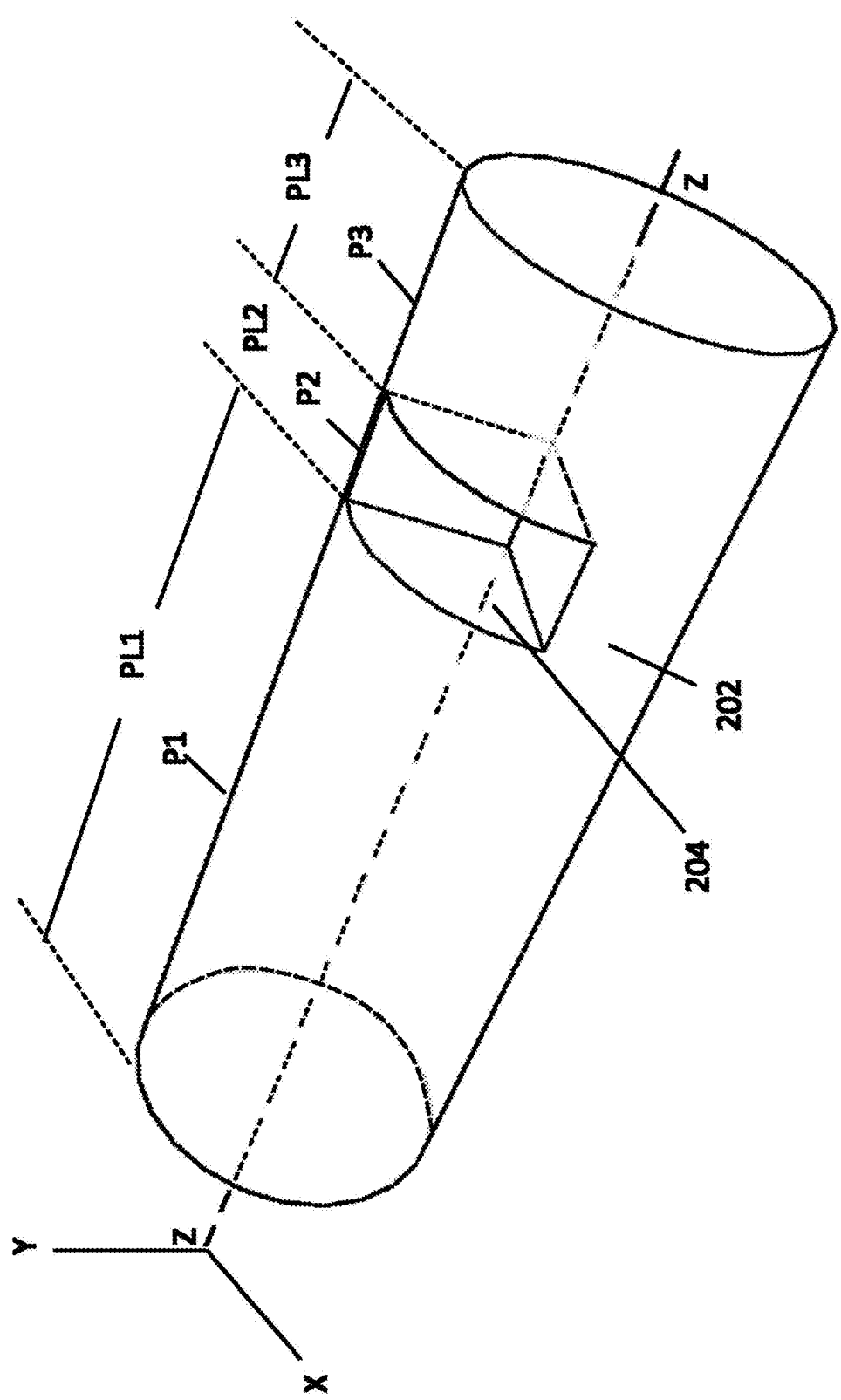
FIG. 5 and FIG. 6 are illustrations showing a same dosage applied to both the posterior and anterior of the patient along portions of the z-length and a varied dosage applied to the posterior and anterior of the patient along another portion of the z-length according to embodiments disclosed herein.
Figure 6:
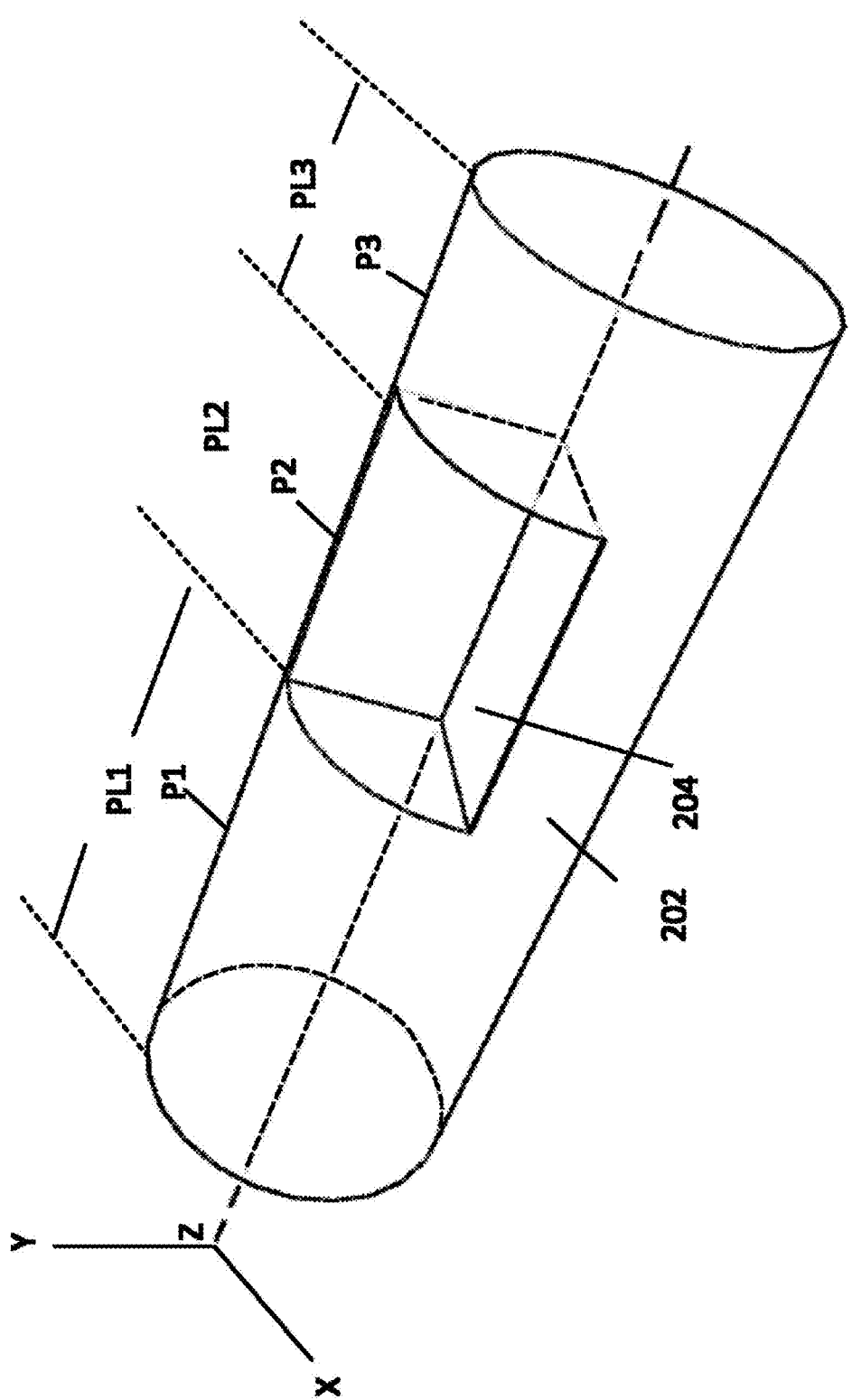

FIG. 5 and FIG. 6 are illustrations showing a same dosage applied to both the posterior and anterior of the patient along portions of the z-length and a varied dosage applied to the posterior and anterior of the patient along another portion of the z-length according to embodiments disclosed herein. FIG. 5 is an illustration showing a dosage region corresponding to a same dosage applied to both the posterior and anterior of the patient along portions P1 and P3 of the z-length and varied dosage regions corresponding to varied dosages applied to the posterior and anterior of the patient along another portion P2 of the z-length according to embodiments disclosed herein. The length PL2 of portion P2 shown in FIG. 6 is greater than the length PL2 of portion P2 shown in FIG. 5. The varied dosage shown in FIG. 5 and FIG. 6 may include dosages applied in the exemplary dosage regions 202 and 204 shown in FIG. 2 and FIG. 4. Embodiments may also include varied dosages applied in dosage regions different from the regions shown in FIG. 2 and FIG. 4.

As shown in FIG. 5, portion P1 extends a length PL1 along the z-length and portion P3 extends a length PL3 along the z-length. Portion P3 extends a length PL3 along the z-length. The lengths PL1, PL2 and PL3 of the portions P1, P2 and P3, the beginning of each of the lengths PL1, PL2 and PL3 of the portions P1, P2 and P3 and/or the ends PL1, PL2 and PL3 of each of the lengths of the portions P1, P2 and P3 may be determined, by for example a control processor, based on locations of radiosensitive organs in the anatomy of a patient. For example, a control processor may determine a location of a radiosensitive organ within the portion P2. The processor may then control the X-Ray dosage by causing a same dosage of the X-Ray radiation to be applied in the x-y plane to a posterior 206 of the patient and to an anterior 208 of the patient P along the length PL1 of portion Pl. The processor may then cause the varied dosage (e.g., first dosage 202 and second dosage 204) of the X-Ray radiation to be applied in the x-y plane along the length PL2 of portion P2 in FIG. 5 (or along the length PL2 of portion P2 in FIG. 6) before causing the same dosage of the X-Ray radiation to again be applied in the x-y plane to a posterior 206 of the patient and to an anterior 208 of the patient P along the length PL3 of portion P3.

The locations of radiosensitive organs in the anatomy of the patient may be determined from different images using various imaging techniques, such as for example, vortex imaging techniques, random forest techniques, deep learning techniques, circle techniques and transforms, such as a Huff transform, to learn and distinguish characteristics of objects and points in an image.

In one embodiment, the location of one or more radiosensitive organs in the anatomy of the patient may be determined from a corresponding location of the radiosensitive portion in one or more images provided from a topogram of the patient prior to applying the X-Ray radiation to the anatomy of the patient in the x-y plane and along the z-axis in the spiral CT scan. For example, the location of eye lenses may be determined from an image provided by the topogram. The location of the eye lenses in the topogram may be determined, for example, by using circle detection techniques to identify circular or near circular orbits around the lenses. In some aspects, a 3D map of a radiosensitive portion (e.g. eye portion) of the anatomy may be constructed to identify a location of the portion of the anatomy from the corresponding location of the radiosensitive portion of the anatomy in the 2D image from the topogram. The varied dosage (e.g., first dosage 202 and second dosage 204) of the X-Ray radiation may then be applied in the x-y plane along a length extending equal to or within a predetermined threshold length greater than the length of the eye orbits along the z-axis.

The topogram facilitates the determination of an accurate location of the radiosensitive portion of the anatomy because the patient does not move between the topogram and the spiral CT scan. Further the topogram is always performed before the spiral scan to determine other system parameters for the individual patient and does not subject the patient to high levels of radiation. Therefore the topogram may be efficiently used to determine location of radiosensitive portions, such as organs, without subjecting the patient to any harmful radiation.

In another embodiment, the location of one or more radiosensitive organs in the anatomy of the patient may be determined from a corresponding location of the radiosensitive portion in one or more images provided from a camera. For example, a structured light camera may be used to determine the location of breasts of a patient.

In other embodiments, the location of one or more radiosensitive organs in the anatomy of the patient may be determined from a location of one or more other portions of the anatomy of the patient. For example, a location of the neck may be determined. A radiosensitive organ, such as a thyroid, may be determined to be within a range of the neck. Accordingly, the location of the thyroid of the patient may be determined from the location of the neck.

Figure 7:
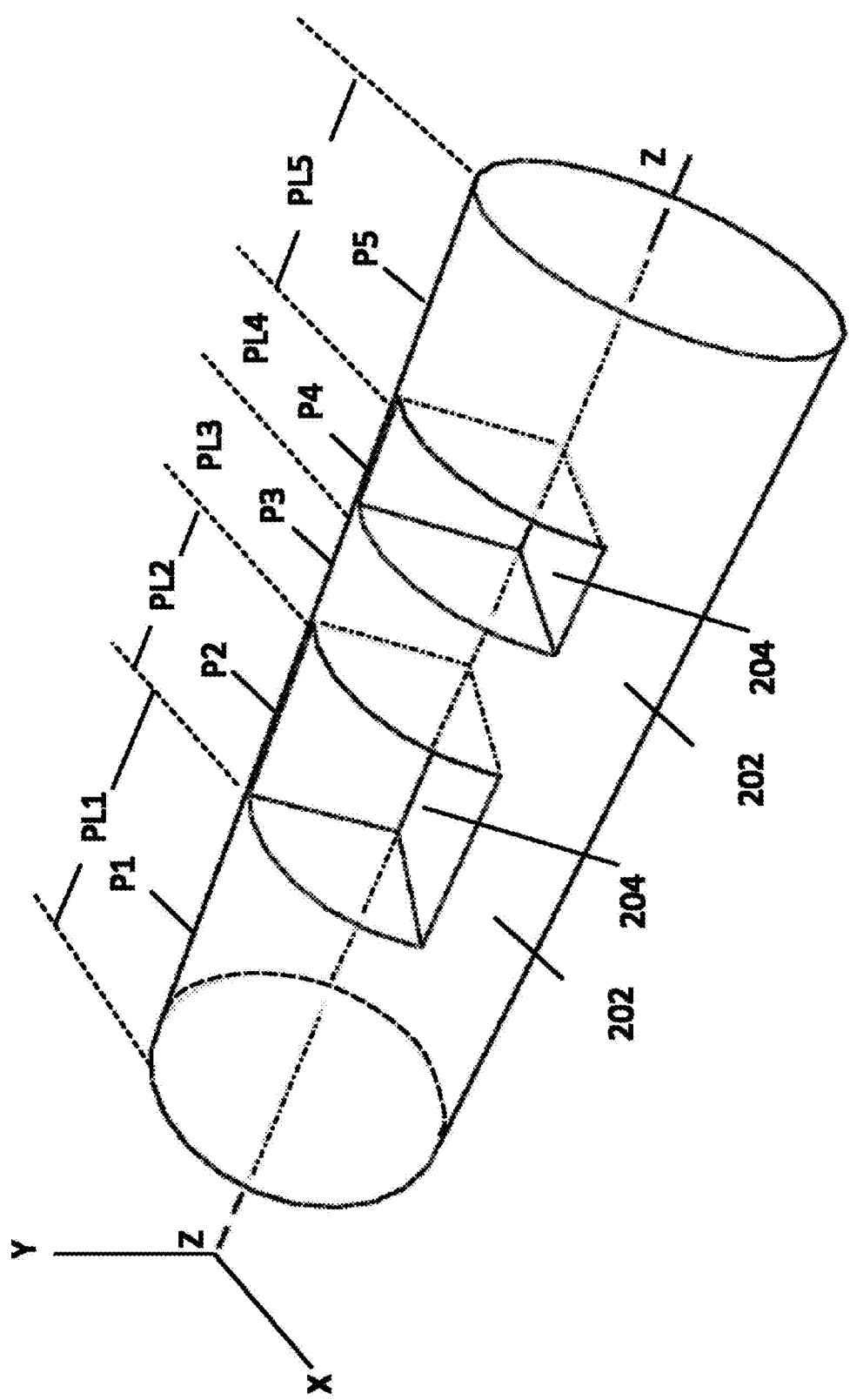
FIG. 7 is an illustration showing a dosage region corresponding to a same dosage applied along portions P1, P3 and P5 of the z-length and varied dosage regions corresponding to varied dosages applied to the posterior and anterior of the patient along portions P2 and P4 of the z-length according to embodiments disclosed herein.

FIG. 7 is an illustration showing dosage regions corresponding to a same dosage applied along portions P1, P3 and P5 of the z-length and varied dosage regions corresponding to varied dosages applied to the posterior and anterior of the patient along portions P2 and P4 of the z-length according to embodiments disclosed herein. The location of more than one radiosensitive organ in the anatomy of the patient may be determined. For example, the location of a first radiosensitive organ having a first length along the z-axis may be determined and a second radiosensitive organ having a shorter length (shorter than the length of the first radiosensitive organ) along the z-axis may be determined. Accordingly, a control processor may control the X-Ray dosage by causing a same dosage of the X-Ray radiation to be applied in the x-y plane to a posterior 206 (shown in FIG. 2) of the patient P and to an anterior 208 (shown in FIG. 2) of the patient P along the lengths PL1, PL3 and PL5 of portions P1, P3 and P5 and may cause the varied dosage (e.g., first dosage 202 and second dosage 204) of the X-Ray radiation to be applied in the x-y plane along a length PL2 of portion P2 for the first radiosensitive organ and along a shorter length PL4 of portion P4 for the second radiosensitive organ.

Conventional systems continuously apply the reduced dosage to the anterior of the patient uniformly along the x-y plane for the z-length of the scan during the anterior view of the patient. Embodiments described herein determine the location of one or more radiosensitive portions of anatomy along the x-y plane and cause the varied dosage of the X-Ray radiation applied along the x-y plane based on the determined location of the radiosensitive portion along the x-y plane. For example, in some embodiments, the location of a first radiosensitive portion of anatomy along the x-y plane may be determined and a location of a second radiosensitive portion of the anatomy along the x-y plane may be determined. Based on the determined locations of the first radiosensitive portion of the anatomy and the second radiosensitive portion of the anatomy, the varied dosage of the X-Ray radiation may be applied the same or differently.

Figure 8:
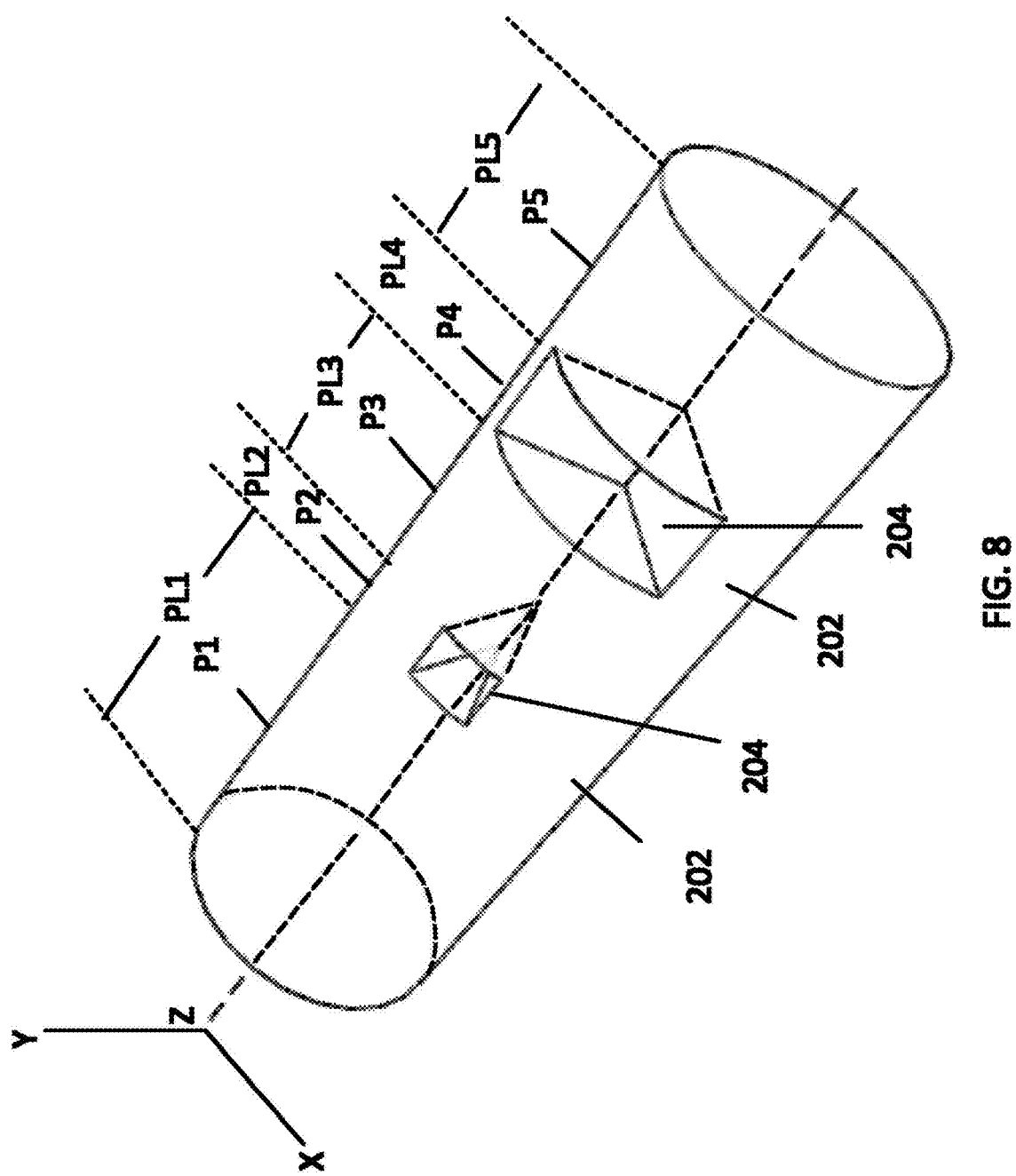
FIG. 8 is an illustration showing varied dosage regions corresponding to varied dosages applied at different ranges of degrees along the x-y plane according to embodiments disclosed herein.

FIG. 8 is an illustration showing varied dosage regions corresponding to varied dosages applied at different ranges of degrees along the x-y plane according to embodiments disclosed herein. Similar to the regions shown in FIG. 7, FIG. 8 also shows dosage regions corresponding to a same dosage applied along portions P1, P3 and P5 of the z-length, a first varied dosage region corresponding to a first varied dosage applied along portion P2 of the z-length and a second varied dosage region corresponding to a second varied dosage applied along portion P4 of the z-length. As shown in FIG. 8, however, the first varied dosage and the second varied dosage are applied along the x-y plane for different ranges of degrees around the z-axis of rotation. These ranges of degrees may be applied differently because of different determined locations of the radiosensitive portions along the x-y plane. For example, the location of the first radiosensitive portion of the anatomy along the x-y plane may be determined to extend along a smaller area of the x-y plane than the second radiosensitive portion of the anatomy. The ranges of degrees shown in FIG. 8 are merely exemplary. Embodiments may include varied dosages corresponding to dosages applied for different ranges of degrees shown in FIG. 8. The number of varied dosage regions shown in FIG. 8 is also exemplary. Embodiments may include any number of varied dosages regions.

As described above with respect to determining the locations of radiosensitive portions along the z-axis, the locations of radiosensitive portions along the x-y plane may be determined from different images using various imaging techniques, such as for example, vortex imaging techniques, random forest techniques, deep learning techniques, circle techniques and transforms, such as a Huff transform, to learn and distinguish characteristics of objects and points in an image.

Some embodiments provide an article of manufacture for controlling radiation dosage of an X-Ray CT system. The article of manufacture may include a non-transitory, tangible computer-readable medium holding computer-executable instructions for performing any of the methods described in the embodiments herein.

The system and processes of the figures presented herein are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. Further, the processes and applications may, in alternative embodiments, be located on one or more (e.g., distributed) processing devices on a network linking the units of FIG. 6. Any of the functions and steps provided in the Figures may be implemented in hardware, software or a combination of both. No claim element herein is to be construed under the provisions of 35 U.S.C. 112, sixth paragraph, unless the element is expressly recited using the phrase "means for."

Although the invention has been described with reference to exemplary embodiments, it is not limited thereto. Those skilled in the art will appreciate that numerous changes and modifications may be made to the preferred embodiments of the disclosure and that such changes and modifications may be made without departing from the true spirit of the disclosure. It is therefore intended that the appended claims covered be construed to all such equivalent variations as fall within the true spirit and scope of the disclosure.

The invention claimed is:

1. A method of controlling radiation dosage of an X-Ray computer assisted tomography (CT) system comprising:
 applying X-Ray radiation to anatomy of a patient along a length of a z-axis in an x-y plane at a plurality of angles during each of one or more 360 degree rotations around the z-axis, the z-axis extending along a length of the patient and intersecting the x-y plane;
 acquiring X-Ray projections of the anatomy of the patient to reconstruct a three dimensional (3D) image of the anatomy; and
 controlling a dosage of the X-Ray radiation applied to the anatomy of the patient by:
  causing a same dosage of the X-Ray radiation to be applied in the x-y plane to a posterior of the patient and to an anterior of the patient at a first portion along the length of the z-axis;
  determining, using one or more images acquired from a camera, a location of a radiosensitive portion of the anatomy of the patient along the length of the z-axis; and causing a varied dosage of the X-Ray radiation to be applied in the x-y plane at a second portion along the length of the z-axis based on the determined location of the radiosensitive portion along the length of the z-axis, the varied dosage comprising a first dosage applied to the posterior of the patient and a second dosage applied to the anterior of the patient, the second dosage applied to the anterior of the patient being less than the first dosage applied to the posterior of the patient.

2. The method of claim 1, wherein the location of the radiosensitive portion of the anatomy of the patient along the length of the z-axis is determined from a corresponding location of the radiosensitive portion in an image acquired from a topogram of the patient prior to applying the X-Ray radiation to the anatomy of the patient in the x-y plane and along the z-axis.

3. The method of claim 1, wherein the location of the radiosensitive portion of the anatomy of the patient along the length of the z-axis is determined from a location of one or more other portions of the anatomy of the patient.

4. The method of claim 1, wherein controlling the dosage of the X-Ray radiation applied to the anatomy of the patient further comprises:
determining the location of the radiosensitive portion of the anatomy along the x-y plane; and
causing the varied dosage of the X-Ray radiation to be applied along the x-y plane based on the determined location of the radiosensitive portion of the anatomy along the x-y plane.

5. The method of claim 4, further comprising causing the varied dosage of the X-Ray radiation to be applied in the x-y plane for a range of degrees of the 360 degrees around the z-axis of rotation based on the determined location of the radiosensitive portion of the anatomy along the x-y plane.

6. The method of claim 1, wherein the X-Ray CT system is one of: (i) a non-spiral X-Ray CT system; and (ii) a spiral X-Ray CT system, and
wherein the same dosage of the X-Ray radiation is applied in the x-y plane perpendicular to the z-axis and the varied dosage of the X-Ray radiation is applied in the x-y plane perpendicular to the z-axis.

7. The method of claim 1, wherein the X-Ray CT system is a spiral X-Ray CT system, and
wherein the same dosage of the X-Ray radiation is applied in the x-y plane at an angle non-perpendicular to the z-axis and the varied dosage of the X-Ray radiation is applied in the x-y plane at an angle non-perpendicular to the z-axis.

8. An X-Ray computer assisted tomography (X-Ray CT) system comprising:
a gantry having an opening configured to receive a patient and a tube-detector system configured to rotate 360 degrees around a z-axis extending along a length of the patient, the tube-detector system of the gantry comprising:
an X-Ray tube configured to apply X-Ray radiation to anatomy of the patient in an x-y plane at a plurality of angles during each of one or more 360 degree rotations along a length of the z-axis that intersects the x-y plane; and
an X-Ray detector disposed opposite the X-Ray tube and configured to detect the X-Ray radiation;
an image processor configured to acquire and process X-Ray projections of anatomy of the patient provided by the tube-detector system to reconstruct a three dimensional (3D) image of the anatomy of the patient; and
a processor configured to control a dosage of the X-Ray radiation applied to the anatomy of the patient by:
causing a same dosage of the X-Ray radiation to be applied in the x-y plane to a posterior of the patient and to an anterior of the patient at a first portion along the length of the z-axis;
determining, using one or more images acquired from a camera, a location of a radiosensitive portion of the anatomy of the patient along the length of the z-axis; and
causing a varied dosage of the X-Ray radiation to be applied in the x-y plane at a second portion along the length of the z-axis based on the determined location of the radiosensitive portion along the length of the z-axis, the varied dosage comprising a first dosage applied to the posterior of the patient and a second dosage applied to the anterior of the patient, the second dosage applied to the anterior of the patient being less than the first dosage applied to the posterior of the patient.

9. The system of claim 8, wherein the location of the radiosensitive portion of the anatomy of the patient along the length of the z-axis is determined from a corresponding location of the radiosensitive portion in an image acquired from a topogram of the patient prior to applying the X-Ray radiation to the anatomy of the patient in the x-y plane for 360 degrees.

10. The system of claim 8, wherein the location of the radiosensitive portion of the anatomy of the patient along the length of the z-axis is determined from a location of one or more other portions of the anatomy of the patient.

11. The system of claim 8, wherein the processor is further configured to control the dosage of the X-Ray radiation applied to the anatomy of the patient by:
determining the location of the radiosensitive portion of the anatomy along the x-y plane; and
causing the varied dosage of the X-Ray radiation to be applied along the x-y plane based on the determined location of the radiosensitive portion of the anatomy along the x-y plane.

12. The system of claim 11, wherein the processor is further configured to cause the varied dosage of the X-Ray radiation to be applied in the x-y plane for a range of degrees of the 360 degrees around the z-axis of rotation based on the determined location of the radiosensitive portion of the anatomy along the x-y plane.

13. The system of claim 8, wherein the X-Ray CT system is one of: (i) a non-spiral X-Ray CT system and (ii) a spiral X-Ray CT system, and
wherein the processor is configured to cause the same dosage of the X-Ray radiation to be applied in the x-y plane perpendicular to the z-axis and the varied dosage of the X-Ray radiation to be applied in the x-y plane perpendicular to the z-axis.

14. The system of claim 8, wherein the X-Ray CT system is a spiral X-Ray CT system, and
wherein the processor is configured to cause same dosage of the X-Ray radiation to be applied in the x-y plane at an angle non-perpendicular to the z-axis and the varied dosage of the X-Ray radiation to be applied in the x-y plane at an angle non-perpendicular to the z-axis.

15. A non-transitory, tangible computer-readable medium holding computer-executable instructions for performing a method of controlling radiation dosage of an X-Ray CT system comprising:

applying X-Ray radiation to anatomy of a patient along the length of a z-axis in an x-y plane at a plurality of angles during each of one or more 360 degree rotations around the z-axis, the z-axis extending along a length of the patient and intersecting the x-y plane;

acquiring X-Ray projections of the anatomy of the patient to reconstruct a three dimensional (3D) image of the anatomy; and controlling a dosage of the X-Ray radiation applied to the anatomy of the patient by:

causing a same dosage of the X-Ray radiation to be applied in the x-y plane to a posterior of the patient and to an anterior of the patient at a first portion along the length of the z-axis;

determining, using one or more images acquired from a camera, a location of a radiosensitive portion of the anatomy of the patient along the length of the z-axis; and causing a varied dosage of the X-Ray radiation to be applied in the x-y plane at a second portion along the length of the z-axis based on the determined location of the radiosensitive portion along the length of the z-axis, the varied dosage comprising a first dosage applied to the posterior of the patient and a second dosage applied to the anterior of the patient, the second dosage applied to the anterior of the patient being less than the first dosage applied to the posterior of the patient.

16. The computer-readable medium of claim 15, wherein the location of the radiosensitive portion of the anatomy of the patient along the length of the z-axis is determined from a corresponding location of the radiosensitive portion in an image acquired from a topogram of the patient prior to applying the X-Ray radiation to the anatomy of the patient in the x-y plane for 360 degrees.

17. The computer-readable medium of claim 15, wherein the location of the radiosensitive portion of the anatomy of the patient along the length of the z-axis is determined from a location of one or more other portions of the anatomy of the patient.

18. The computer-readable medium of claim 15, wherein controlling the dosage of the X-Ray radiation applied to the anatomy of the patient further comprises:

determining the location of the radiosensitive portion of the anatomy along the x-y plane; and causing the varied dosage of the X-Ray radiation to be applied along the x-y plane based on the determined location of the radiosensitive portion of the anatomy along the x-y plane.

* * * * *